United States Patent [19]

Naraghi

[11] Plant 4,466

[45] Oct. 23, 1979

[54] ALMOND TREE

[76] Inventor: Hashem Naraghi, 17428 Keyes Rd., Denair, Calif. 95316

[21] Appl. No.: 964,885

[22] Filed: Nov. 30, 1978

[51] Int. Cl.[2] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is large, dense, vigorous, robust, and extremely bushy with a stocky trunk, spreading with slender branches, abundantly foliated with large, ovate, acutely pointed, glossy leaves darker green than average, blooms heavily with white, pink-centered flowers, and is a regular and very heavy producer of large, medium brown, well distributed nuts having a large, medium brown kernel.

6 Drawing Figures

BACKGROUND OF THE VARIETY

1. Field of the Discovery

The present new and distinct variety of almond tree is embraced by Class 30, Plants, of the United States Patent Office Manual of Classification.

2. Prior Varieties

Among the existent varieties of almond tree which are known to me, and mentioned herein, are Nonpareil and Mission (both unpatented) and Merced (U.S. Plant Pat. No. 1,730).

ORIGIN OF THE VARIETY

While the origin of the present variety of almond tree is unknown, it was discovered by me—as a probable mutation and growing as an individually distinct tree—in my orchard of almond trees located near Denair, Stanislaus County, Calif.; such orchard including Nonpareil, Mission, and Merced almond trees.

My attention was particularly attracted to such individually distinct tree by reason of its extremely bushy tree form, the retention in full green color of the leaves substantially beyond the reasonable duration of other varieties, and by a substantially heavier crop of nuts than borne by the Nonpareil. Upon discovery of such individually distinct tree, and in view of its apparent commercial value, I determined to effect asexual reproduction of the variety.

ASEXUAL REPRODUCTION OF THE VARIETY

The present variety of almond tree was asexually reproduced, on my behalf and by a commercial nursery, by grafting and budding, and such asexual reproductions—in maturity—ran true to the original tree in all respects.

SUMMARY OF THE VARIETY

The herein-claimed variety of almond tree is large, dense, vigorous, robust, and extremely bushy with a stocky trunk, spreading with slender branches, abundantly foliated with large, ovate, acutely pointed, glossy leaves darker green than average, blooms heavily with white, pink-centered flowers, and is a regular and very heavy producer of large, medium brown, well distributed nuts having a large, medium brown kernel.

The herein-claimed variety of almond tree is further characterized—in addition to time-extended color retention of the leaves—by leaves which are larger, darker green, and more glossy than is average for existing almond varieties; the leaves effectively withstanding insects and resisting diseases normal to other varieties of almond trees.

The herein-claimed variety of almond tree is still further characterized by the bearing of nuts which—while generally similar to the Nonpareil—are borne regularly in a heavier crop; the kernels being slightly lighter in color and of larger size than the Nonpareil. "Blank" nuts and "gummy" nuts have not been observed.

BRIEF DESCRIPTION OF THE DRAWING

The drawing is an illustration, by photographic reproduction in color, of a twig with leaves, and, separately, nuts out of hull, and kernels out of shell.

DESCRIPTION OF THE VARIETY

The botanical details of this new and distinct variety of almond tree—with color definitions (except those in common color terms) referenced to Maerz and Paul Dictionary of Color—are as follows:

Tree:
- *Density.*—Dense.
- *Size.*—Large.
- *Vigor.*— Vigorous.
- *Form.*—Extremely bushy.

Trunk:
- *Form.*—Stocky.
- *Texture.*—Medium.

Branches:
- *Form.*—Slender.
- *Texture.*—Smooth.
- *Branching habit.*—Spreading.
- *Color.*—New wood — Green. Mature wood — Gray.

Foliage:
- *Quantity.*—Abundant.

Leaves:
- *Size.*—Large. Average length — 4". (Average width).
- *Shape.*—Ovate, acutely pointed.
- *Thickness.*—Thin.
- *Texture.*—Smooth.
- *Margin.*—Finely serrate.
- *Petiole.*—Long, medium thickness.

*Color.*—Top side — Cress green (22-K-6), under side — Slightly darker green (22-L-7).

Bloom:

*Amount of bloom.*—Heavy.

*Color.*—White, pink-centered.

*Blooming period.*—February 20—first week of March, medium, as compared to other varieties, same as Nonpareil.

Crop:

*Bearing.*—Regular bearer.

*Productivity.*—Very heavy.

*Distribution of nuts on tree.*—Well distributed.

*Harvest period.*—September — same as Nonpareil.

*Tenacity.*—Easy to harvest. Easy to hull.

Hull:

*Outer surface.*—Smooth.

*Form.*—Regular.

*Thickness.*—Thick.

*Flesh.*—Fleshy.

*Suture.*—Ridged.

*Color.*—Dark green with silvery sheen.

*Dehiscence.*—Opens freely.

*Splitting.*—Along suture.

Nut:

*Size.*—Large, Average length — 1¼". Average width (including wing) — 7/8". Average thickness — ½".

*Form.*—Width/Thickness — Plump.

*Shell.*—Paper. Outer shell — Crumbly. Inner shell — Soft, poorly sealed.

*Color.*—Macaroon brown (12-H-7).

*Pits.*—Small, few, round.

*Base.*—Dorsally oblique.

*Stem scar.*—Small, acute.

*Apex.*—Acute, prolonged at tip.

*Wing.*—Narrow, thin, tapered toward base.

*Inner surface.*—Dark colored.

*Ventral streak.*—Dark, narrow, long, point acute.

*Percentage of kernel to nut.*—65%–70%.

Kernel:

*Size.*—Large. Average length — 1". Average width — ½". Average thickness — 5/16". Average weight — 1 gram.

*Form.*—Length/Width — Elongated, wedge. Width/Thickness — Plump.

*Base.*—Square.

*Stem scar.*—Small, acute.

*Apex.*—Acute, sharp, blunt, tip recurved.

*Texture.*—Smooth.

*Pellicle.*—Thin.

*Pubescence.*—Veined.

*Color.*—Centennial brown (13-K-8).

*Number of doubles.*—None.

*Defective kernels.*—None.

*Flavor.*—Sweet.

*Quality.*—Very good.

Resistance to insects and diseases: Resistant to almond mite, shot-hole fungus, red spider, and brown rot. No unusual susceptibilities noted.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, particularly characterized by a tree which is vigorous, robust, and extremely bushy; by time-retention of green leaf color—darker than average—beyond normal expectancy, and —in comparison to the Nonpareil—by heavier crops of nuts whose kernels are slightly lighter in color and of larger size.

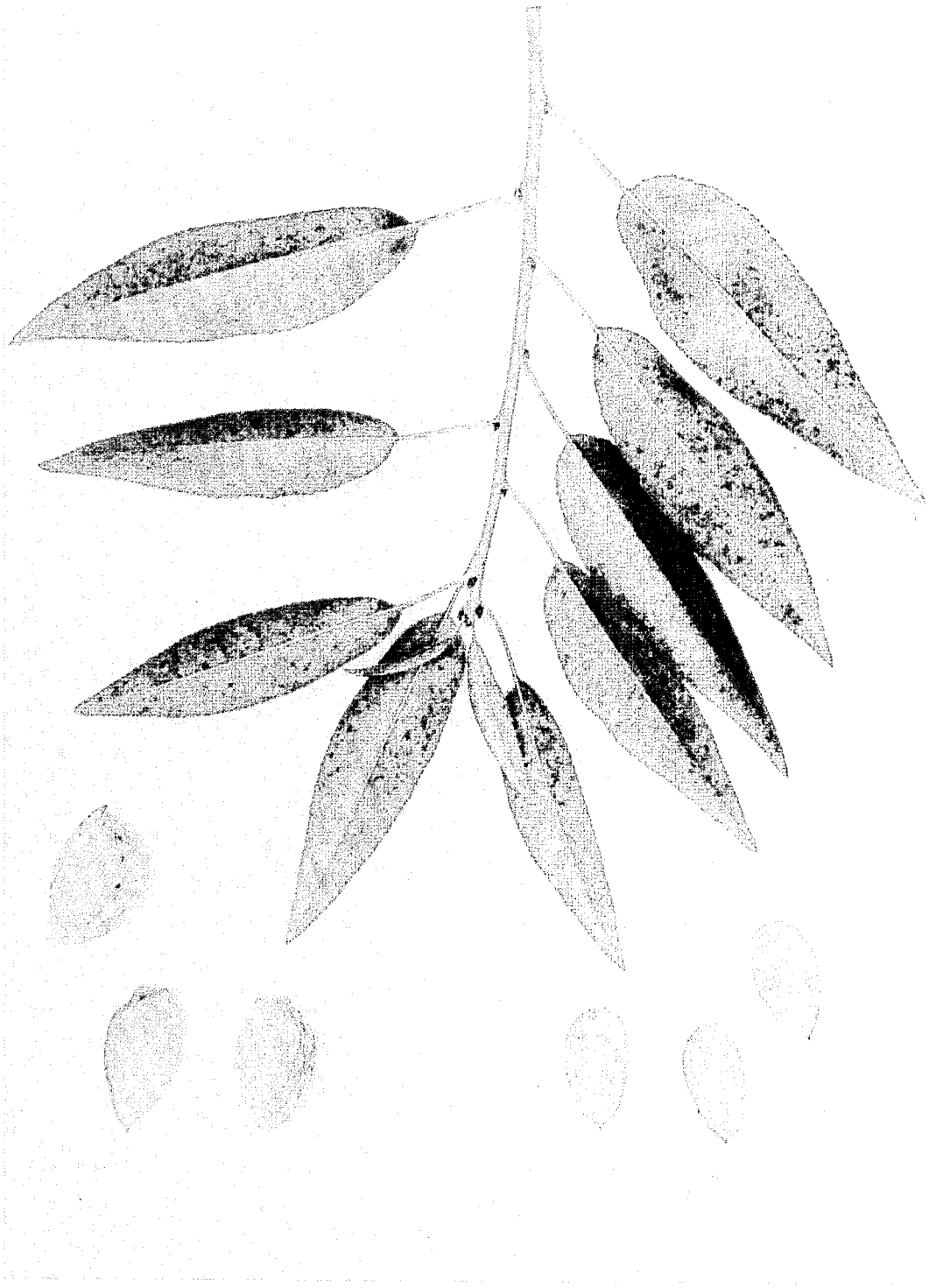

* * * * *